United States Patent [19]

Schön

[11] Patent Number: 5,578,006
[45] Date of Patent: Nov. 26, 1996

[54] SUCTION CATHETER

[75] Inventor: Rudolf Schön, Am Kümpel 18, D 53127 Bonn, Germany

[73] Assignee: Rudolf Schön, Bonn, Germany

[21] Appl. No.: 307,627

[22] PCT Filed: Mar. 19, 1993

[86] PCT No.: PCT/EP93/00672

§ 371 Date: Nov. 14, 1994

§ 102(e) Date: Nov. 14, 1994

[87] PCT Pub. No.: WO93/18801

PCT Pub. Date: Sep. 30, 1993

[30] Foreign Application Priority Data

Mar. 20, 1992 [DE] Germany ............... 42 08 912.3

[51] Int. Cl.$^6$ .................................................. A61M 11/00
[52] U.S. Cl. .......................... 604/93; 604/264; 604/280; 604/902
[58] Field of Search ............... 604/93, 264, 266, 604/268, 280, 283, 313, 314, 315, 316, 902, 118, 119

[56] References Cited

U.S. PATENT DOCUMENTS

| 1,626,839 | 5/1927 | Kallmeyer | 604/264 |
| 2,504,557 | 4/1950 | Lumian | 32/33 |
| 3,753,292 | 8/1973 | Hutson | 32/33 |
| 3,848,604 | 11/1974 | Sackner | 128/350 R |
| 3,945,385 | 3/1976 | Sackner | 128/350 R |
| 4,769,016 | 9/1988 | Labianca | 604/266 |

*Primary Examiner*—John D. Yasko
*Assistant Examiner*—Ronald K. Stright, Jr.
*Attorney, Agent, or Firm*—Antonelli, Terry, Stout & Kraus

[57] ABSTRACT

A suction catheter for sucking mucus and other fluids from the tracheobronchial area of a patient, has a flexible tube with at least one through lumen extending from a proximal end to a distal end. A thickened area is provided adjacent to the distal end in the form of a cylindrical portion for promoting guidance of the catheter in the tracheobronchial area of a patient. In addition, the lumen is provided with a funnel-shaped enlarged outlet.

21 Claims, 3 Drawing Sheets

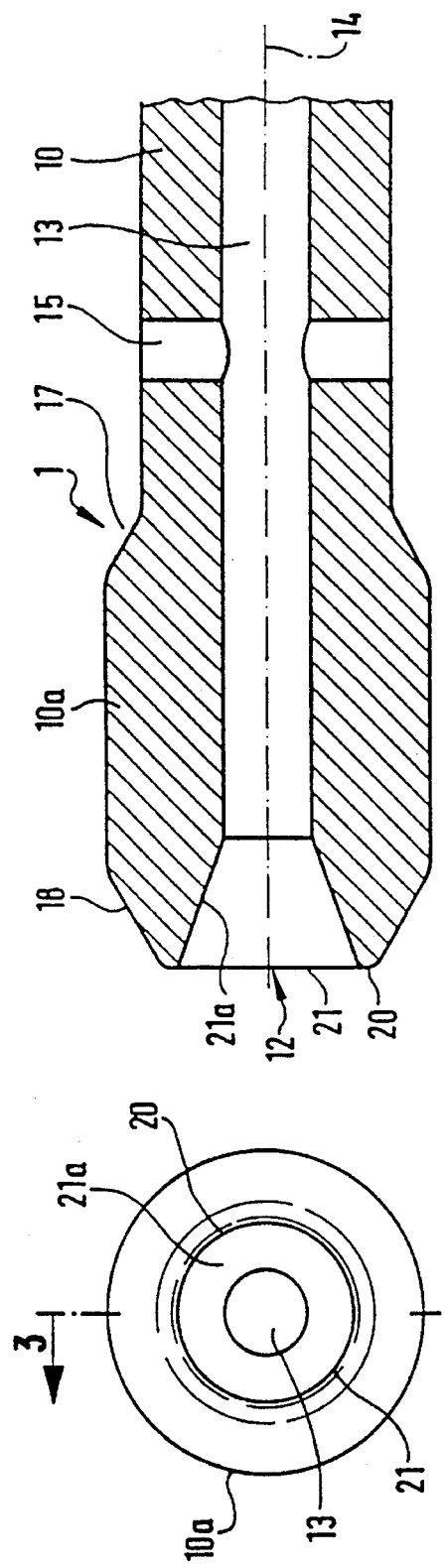
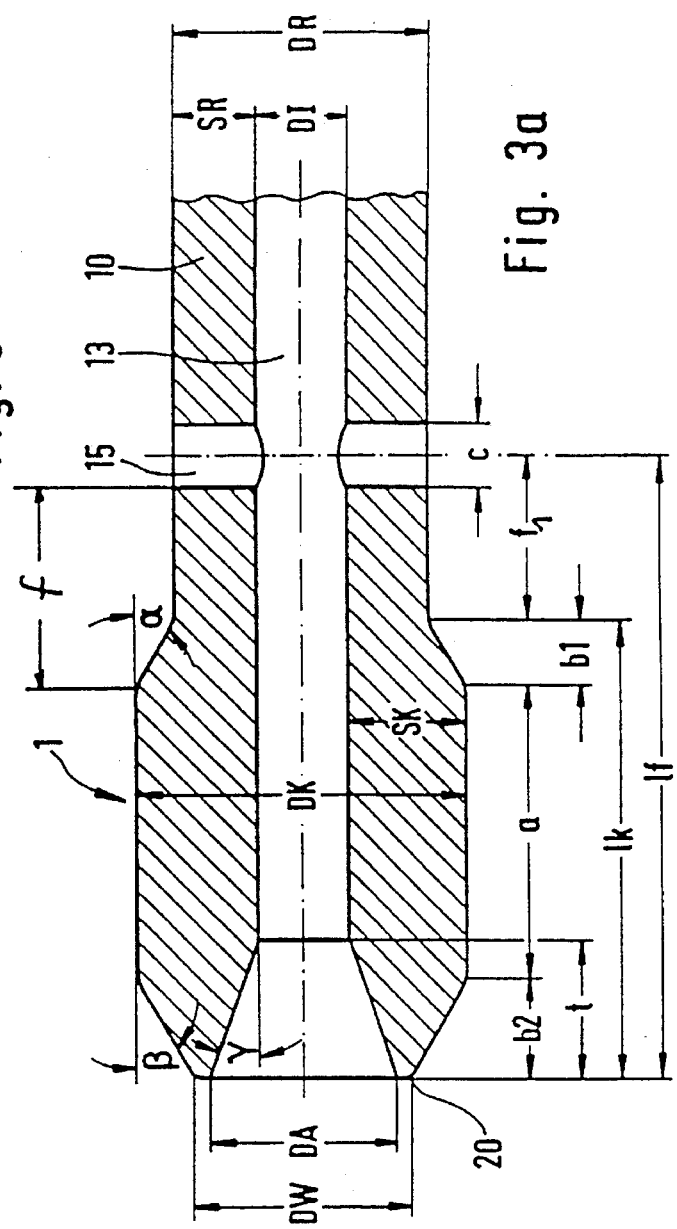

SUCTION CATHETER

The invention relates to a suction catheter for sucking mucus and other fluids from the tracheobronchial space of a patient, with a flexible catheter tube having at least one through lumen, said tube having a proximal end and a distal end and being connectable at the proximal end with a connector or the like, with radial vent openings extending into the lumen being formed in the catheter tube in the vicinity of the distal end.

Suction catheters of the type according to the species are known for example from DE-AS 2364119.

U.S. Pat. No. 2,130,406 teaches a suction snorkel for sucking saliva out of the oral cavity for dental purposes, said snorkel being thickened externally at its distal end, with the thickening being interrupted on the exterior by notches running radially.

A similarly designed suction snorkel for dental purposes is shown in U.S. Pat. No. 2,574,135. In this case, the end of the snorkel is thickened in the shape of a cylindrical piston and has external notches extending into the distal outlet opening.

When sucking mucus out of the tracheobronchial space by means of suction catheters, a constant vacuum during suction can result in serious injury to the mucous membrane. Firstly, there is the danger of the suction catheter sticking to the mucous membrane and of the latter being pulled away directly by it. Suction catheters are usually provided with at least one side hole in addition to the distal outlet opening at the end. If the suction catheter comes into close contact with the mucous membrane, it lifts the mucous membrane by means of the vacuum and invaginates it into these side holes or even into the outlet opening. The resultant injuries serve as breeding sites for bacteria and lead to edema, etc.

In the catheter known from DE-AS 2364119 a rounded annular bead is formed at the distal end of the suction catheter to avoid injury to the mucous membrane, said bead projecting radially at the end of the catheter over the circumference of the catheter. This annular bead serves to center the catheter within the trachea and is also intended to produce a laminar air cushion so that it does not come in contact with the wall of the trachea, nor can any mucous membrane be sucked into the catheter. It has been found however that drawing mucous membrane into the radial lateral openings of the catheter cannot be avoided in all cases. In addition, there is often the problem of the distal outlet opening becoming clogged with mucus.

The goal of the invention is to improve the design of the known suction catheter in such fashion that clogging of the distal end by mucus during suction is avoided and the adhesion to or drawing of mucous membranes into the distal outlet opening or the lateral openings in the vicinity of the distal end of the catheter is reliably avoided.

To achieve this goal it is proposed to improve the suction catheter according to the species in such fashion that the lumen expands like a funnel at the distal end of the catheter tube of the suction catheter, and a distal outlet opening of the lumen that is enlarged relative to the cross section of the lumen is formed, and, in the distal end area of the catheter tube, in the area between the ventilation openings and the distal end, a thickened area is formed in the shape of a cylindrical piston with transition zones abutting it on both sides and tapering toward the proximal end of the catheter tube or toward the distal end.

In addition to the funnel-shaped expansion of the outlet of the lumen at the distal end of the suction catheter, it is also possible to expand the funnel and/or the lumen walls by means of notches impressed into the walls and running in the axial direction. When the distal outlet opening of the lumen is expanded either by means of a funnel-shaped expansion or by means of notches, the notches can extend for the same distance, for a shorter distance, or for a greater distance than the funnel-shaped expansion in the axial direction into the lumen.

The enlargement of the outlet opening according to the invention in conjunction with the thickened area near the distal end of the suction catheter that serves as a sealing and guiding piston will surprisingly avoid clogging of the distal end of the suction catheter. The design of the catheter tube at the distal end also contributes to this which, seen in an axial section, terminates with a taper at the transition zone.

Surprisingly, it has been found that even with very viscous secretions that must be drawn up from the bronchial area with the aid of the suction catheter, the secretion does not clog the distal outlet opening of the suction catheter when the vacuum is applied but is drawn off smoothly. At the same time, adhesion of the suction catheter or distal end area to the mucous membranes by suction is avoided. Any invagination of the mucous membranes, even in the slightest, is avoided. This is because the funnel-shaped expansion of the lumen toward the distal outlet opening, results in improved suction of mucus and its conveyance into the lumen. The distal outlet opening of the suction catheter can be expanded according to the invention by means of additional notches in partial areas, said notches being impressed into the walls of the funnel-shaped expansion. These notches are made relatively small, but are formed over the expanded outlet area into the normal lumen area. In a preferred embodiment, the notches extend for the same distance, as viewed from the distal end of the catheter tube, as a funnel similarly formed in the lumen in the axial direction.

By shaping the distal end area of the suction catheter as a cylindrical piston, a flush guidance of the suction catheter into the airways, such as the trachea, is accomplished, which also prevents the mucous membranes from being drawn into the ventilation openings of the catheter that follow in the direction of the proximal end of the suction catheter. Clogging of the ventilation openings by mucus is also avoided.

In this manner, damage to the submucosa and mucosa are avoided in this area as well. In all known suction catheters that have no annular bead at the distal end, damage persistently occurs to the mucous membranes in the vicinity of the ventilation openings of the suction catheter. Suction catheters with an annular bead on the distal end also prevent the mucous membranes from being drawn in in the vicinity of the radial ventilation openings when the distal outlet end is clogged by mucus.

The present invention provides a remedy in this regard, since, by virtue of a special design in the vicinity of the outlet opening, it prevents clogging of the latter with viscous secretions, i.e. permits smooth suction and thus prevents the suction catheter from being drawn against the mucous membranes through the ventilation openings. It has been found that air is drawn in through the radial ventilation openings, so that lung segments do not collapse when secretions are being sucked out of the bronchial area. Maintaining a certain distance between the ventilation openings and the thickened areas formed in the distal end area of the suction catheter, in the form of a cylindrical piston part, is important to maintain this ventilation. This distance between the ventilation openings of the suction catheter and the beginning of the cylindrical piston should be less than 7 mm. This distance must be maintained independently of the size of the suction catheter.

An important design for the suction catheter according to the invention consists in the fact that the thickened area formed in the distal end area of the suction catheter, in the form of a cylindrical piston, determines by its outside diameter the size of the suction catheter in CH (Charr) according to the ISO standard, and the catheter tube that abuts the proximal end of the suction catheter is made with an outside diameter that is smaller, in other words smaller than the cylindrical piston and the distal end area. Formerly, the size of the suction catheter in Charriere was usually determined by the outside diameter of the long catheter tube, also for example in suction catheters according to DE-AS 2 364 119.

Therefore, according to the invention, the outside diameter of the cylindrical piston of the thickened area within the distal end area is used in conjunction with the diameter of the through lumen used for suction to determine the size of the suction catheter measured in CH according to the ISO standard.

The design of the distal end area according to the invention with a cylindrical piston that projects with its outside diameter beyond the rest of the catheter tube can also be used in suction catheters with two lumina, like those described for example in German Patent 3 608 943.

Preferred embodiments of a suction catheter with a suction catheter are formed by a thickened area in the shape of a cylindrical piston within the distal end area of the catheter tube, which guides the suction catheter when it is inserted into the tracheobronchial system of a patient.

The size of the piston on the one hand and the size of the funnel on the other are critical for reliable function of the suction catheter according to the invention as an atraumatic catheter.

To prevent clogging of the distal outlet opening of the suction catheter, an expansion of the lumen at the outlet end of the catheter tube according to the invention is proposed. This expansion of the lumen can be made as funnel-, cone-, or trumpet-shaped or can be formed by notches impressed into the lumen walls and extending up to the distal end of the catheter tube, or by a combination of a funnel-shaped expansion and notches. Several embodiments of a suction catheter of the type according to the species have an expanded distal outlet opening.

The preferred dimensions for the design of the suction catheter according to the invention reflect the standardized suction catheter sizes from 8 CH to 18 CH, with conventional manufacturing tolerances taken into account. The catheter tube for the suction catheter is manufactured from suitable sterilizable thermoplastic plastics which are extrudable by extrusion with subsequent molding.

The suction catheter or catheter tube is made of a nontoxic, flexible, bendable material such as natural or synthetic rubber, polypropylene, polyethylene, polyvinyl chloride, or polyamides.

The stiffness of the material can be chosen so that even in long suction catheters which as a rule have a length between 50 and 65 cm at the stated sizes of 8 CH to 18 CH, sufficient stiffness and resistance to kinking are achieved, even with very thin wall thicknesses of the catheter tube.

The length a of the cylindrical piston should be sufficient to permit, depending on the size of the catheter, a sufficiently flush fit and guidance of the catheter or end of the catheter in the airways. The transition zones abutting on both sides form conical or approximately conical or rounded transitions from the cylindrical piston to the catheter tube which on one side extends directly into an axial end bead of the catheter tube at the distal outlet opening and on the other side extends up to the proximal end. These transitions are gently sloped and preferably are made with the same angles and are of approximately equal length on both sides.

By virtue of the cooperation of the funnel formed at the distal end of the lumen and the outlet opening whose cross section is consequently enlarged relative to the lumen cross section on the one hand and the external transition zone from the piston to the distal end of the catheter tube with a conical taper or rounded taper or rounded taper of the cross section of the catheter tube on the other hand, the distal end of the catheter tube terminates with a taper in a rounded end that has a smaller outside diameter than the piston of the thickened area of the catheter tube. This end permits a gentle, soft introduction of the suction catheter into the airways of a patient.

The proximal end of the suction catheter can be provided with a connector, for example a funnel, but can also be equipped with other parts or connected to devices. The proximal end of the suction catheter can itself also be made with a conical expansion.

The distal end area of the suction catheter is usually provided in the straight lengthwise part of the catheter tube, but can also be bent one or more times relative to the lengthwise axis of the suction catheter. In such suction catheters, the thickened area for guiding the suction catheter is made within the distal end area in front of the bent end part, i.e. in the straight part of the catheter tube.

The invention will now be described in greater detail with reference to an embodiment shown in the drawing.

FIG. 2 is a top view of the distal end of the suction catheter in FIG. 1, on an enlarged scale;

FIG. 3 is a section taken along line 3—3 according to FIG. 2 for the distal end area of the suction catheter;

FIG. 3a is FIG. 3 with additional information on the dimensions of the suction catheter;

Figure 1:
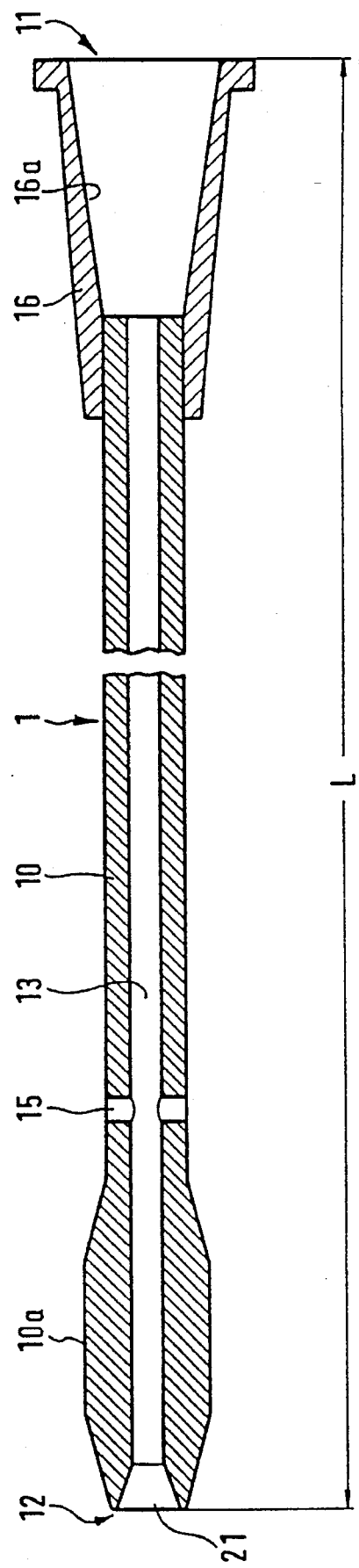
FIG. 1 is a schematic diagram in lengthwise section, not to scale, of a suction catheter.

FIG. 1 shows schematically a suction catheter 1 for sucking secretions and other fluids out of the tracheobronchial space of a patient, said catheter being insertable through the trachea of the patient into the bronchial area. In the example shown, the suction catheter is permanently connected at its proximal end 11 with a connector 16, for example a funnel with an inner funnel 16a. The suction catheter can also be connected with other connectors. Suction catheter 1 comprises catheter tube 10, formed within the distal end area with a thickening in the shape of a cylindrical piston 10a. The single through lumen 13 formed in the catheter tube of suction catheter 1 terminates at distal end 12 in distal outlet opening 21. Suction catheters of the type shown have a length L usually between approximately 50 and 65 cm. The inside diameter of through lumen 13, for example at a catheter size CH 10, is 1.54 mm and at a catheter size CH 16, 3.0 mm. Suction catheter 1 according to FIG. 1 according to the invention has in the distal end area a piston-shaped thickening with respect to the rest of catheter tube 10, namely in the form of cylindrical piston 10a. The outside diameter used as the basis for determining the standard size of suction catheter 1 according to the invention is that of piston 10a as the thickest part of the area of the catheter tube to be inserted into the tracheobronchial space. The outside diameter of catheter tube 10 abutting the thickened area 10a, 17, 18 extending to proximal end 11 of the suction catheter is made smaller than the outside diameter 10a of the piston, i.e. catheter tube 10 is smaller than piston 10a.

Piston 10a of the suction catheter is abutted by ventilation openings 15 relatively close to proximal end 11 of the suction catheter, said openings extending radially through the wall of catheter tube 10 and connecting lumen 13 with the environment. Here ventilation openings 15 are arranged as holes uniformly distributed over the circumference of catheter tube 10, for example two or four ventilation openings 15.

In FIGS. 2 to 3a the distal end area of suction catheter 1 according to FIG. 1 is shown enlarged and the designs according to the invention will now be described in greater detail.

The club-shaped design of the distal end area with cylindrical piston 10a is clearly evident from the lengthwise section through the distal end area of suction catheter 1 in FIG. 3. Cylindrical piston 10a falls away to both sides, i.e. both toward distal end 12 and toward the proximal end through a conical transition zone 18 and 17. In distal end area 12, transition zone 18 blends directly into rounded end 20 delimiting distal outlet opening 21. Transition zone 17 toward the proximal end blends with catheter tube 10, i.e. its outside wall. All transitions are made smooth and rounded.

Through lumen 13, running coaxially in the lengthwise axis 14 of suction catheter 1, is expanded in the manner of a funnel toward distal end 12. This funnel-shaped expansion 21a terminates in outlet opening 21. Outlet opening 21 of through lumen 13 at the distal end 12 of suction catheter 1 is hence larger in cross section than the cross section of lumen 13. The funnel-shaped expansion of the lumen of the catheter tube is delimited by walls that are straight or slightly rounded. Outlet opening 21 is delimited by rounded end 20 of the catheter tube, which forms the rounded axial end of the catheter tube. This annular axial bead 20 externally merges through a conical transition zone 18 directly with cylindrical piston 10a. Viewed in cross section, the bead is made to taper conically on both sides.

In the proximal direction, catheter tube 10 abuts cylindrical piston 10a of the distal end area following conical transition zone 17 with tapering, and immediately thereafter ventilation openings 15, connecting lumen 13 with the environment, are also provided in the walls of the catheter tube. When suction catheter 1 is introduced into a bronchial system for suction, and a vacuum is applied, secretion is drawn toward distal outlet opening 21 from the bronchial area. The funnel abutting outlet opening 21 prevents clogging of outlet opening 21 and of lumen 13 with viscous secretion since because of the funnel-shaped expansion, in addition to the secretion an air stream is drawn in, so that the viscous secretion is drawn into lumen 23 and can be carried away there. The funnel-shaped expansion of the distal end of lumen 13, in conjunction with the external guidance of the catheter by means of piston 10a, prevents the clogging or plugging of the distal end of the lumen with secretion. Ventilation is also permitted in the area of the ventilation openings, so that suction of the mucous membranes, i.e. adhesion thereof and hence damage thereto is prevented here as well in the lateral area, especially by the free space between piston 10a and catheter tube 10.

The design of tapered end 20 of the catheter tube at outlet opening 21 prevents clogging by secretion.

For proper function of the suction catheter provided according to the invention with a distal end area that is thickened in the form of a piston, the dimensions of the piston and the funnel-shaped expansion are important. In FIG. 3a the preferred dimensions according to the invention are given. Angles α and β for the roughly conical transitions of cylindrical piston 10a in the direction of the distal end 12 and the direction of the proximal end, i.e. toward catheter tube 10, measure between 10° and 10° and should have rounded transitions. Inside diameter DI for catheter sizes 8 to 18 CH is between 1.0 and 4.0 mm with an outside diameter DK between 2.7 and 6.1 mm plus manufacturing tolerances measured in the area of the cylindrical piston at the distal end area of the suction catheter. This produces wall thicknesses SK of about 0.7 to 1.5 mm in the vicinity of the cylindrical piston. The outside diameter of catheter tube 10 DR that is tapered relative to piston 10a is approximately 1.7 to 5.1 mm, resulting in wall thicknesses SR of approximately 0.3 to 0.9 mm for the catheter tube. Diameter c of the ventilation openings is between 0.25 and 0.8 mm. The depth t of the funnel-shaped expansion should be 2 to 4 mm, and the diameter DA of the outlet opening at the outlet, i.e. in the vicinity of end bead 20, should be about 1.25 to 4.3 mm, in other words approximately 0.2 to 0.7 mm larger than the respective corresponding inside diameter of lumen 13. The outside diameter DW of end bead 20 should be 0.4 to 0.8 mm larger than the diameter DA of the outlet opening. The smaller values should always be associated with the smaller CH sizes of the suction catheter.

The lengths b1, b2 of transition zones 17 and 18 of the distal end area, i.e. from piston 10a to the areas should preferably be made the same, with these lengths being approximately 1.5 mm to 3.0 mm.

The length a of cylindrical piston 10a should be at least 3 mm to a maximum of 5.0 mm and should preferably be in the range from about 3.0 to 4.5 mm. The space between piston 10a and ventilation openings 15 is important for sufficient ventilation through ventilation openings 15 with the suction catheter inserted into the bronchial system, in other words space f or f1. Space f1 is preferably chosen to be constant for all the catheters, preferably approximately 2.0 to 3.0 mm. The total length Lf of the distal end area designed according to the invention from the distal end to the bore axis of ventilation openings 15, corresponding to catheter sizes of CH 8 to CH 18, should preferably likewise be constant and should be between 9 and 12 mm, preferably 10 mm. Length lk of area 17, 10a, 18 of the catheter tube which is thickened relative to catheter tube 10 is therefore approximately 7–9 mm.

A suction catheter CH 12, with a design according to the invention, has the following dimensions for example (manufacturing tolerances can be added): DI 2.0 mm, DR 3.0 mm, DK 4.0 mm, DA 2.31 mm, DW 3.0 mm, t 3.25 mm, a 4.2 mm, b1, b2 1.65 mm, lk 7.5 mm; f1 2.5 mm; lf 10 mm, α/β 17°; c 0.8 mm.

Depending on the standard and the design of this suction catheter, it is also possible to make designs and dimensions in a manner according to the invention that differ from the above-mentioned dimensions and designs of the suction catheter.

Figure 5:
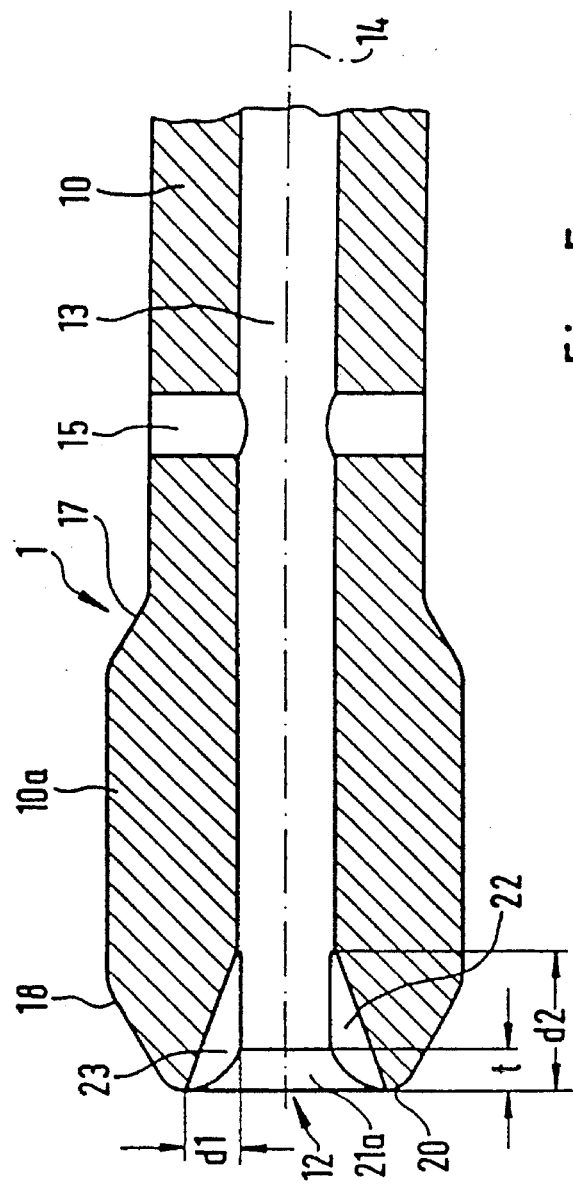
FIG. 5 is a section taken along line 5—5 according to FIG. 4.
Figure 6:
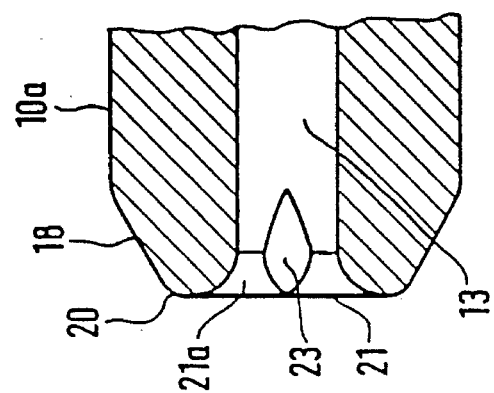
FIG. 6 is a section taken along line 6—6 in FIG. 4 for the distal end area.
Figure 4:
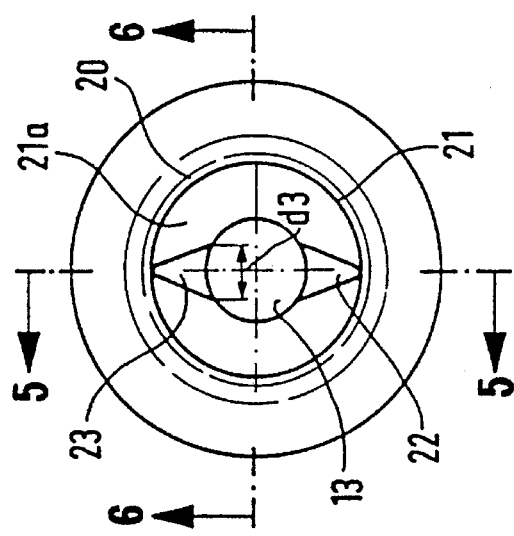
FIG. 4 is a top view of another embodiment of the distal end area of the suction catheter.

FIGS. 4 to 6 show a suction catheter 1 according to the invention whose distal end area has a small funnel-shaped expansion 21a as well as additional notches 21, 22 running axially that are impressed into funnel 21a and the wall that delimits lumen 13.

Distal outlet opening 21 forms a circular surface whose cross section is larger than the cross section of lumen 13. This distal outlet opening 21 is expanded radially by additional notches 22, 23 in partial areas. These notches 22, 23, uniformly distributed over the circumference, two notches opposite one another for example as shown or two additional notches offset with respect to them by 90°, deepen the funnel of the outlet opening at two points in the radial direction. These notches 22, 23 however not only run in the area of the funnel of outlet opening 21 but also extend over the catheter in the axial direction into lumen 13. This is also evident from the view in FIG. 4.

The notches made in the area of the distal outlet of lumen 13 are intended to have a depth d1, measured from the lumen wall in the radial direction from d1, of approximately 0.1 to 0.3 mm and a length d2, measured in the axial direction from the distal end, of approximately 2 to 4 mm. The width d3 of the notches (see FIG. 2) in any event is not intended to be less than the diameter of lumen 13, in particular approximately ½ to ¼ of diameter DI of lumen 13.

The remaining design and dimensions of the suction catheter according to FIGS. 4 to 6 correspond to those of the suction catheter according to FIGS. 2 to 3a.

With the suction catheter designed according to the invention, i.e. the design of the distal end area, all injuries to the mucous membranes during suction as well as clogging of the suction catheter with secretions are avoided.

It is also possible to avoid expanding the outlet end of the lumen of a suction catheter according to FIG. 1 and to guide the catheter tube within the tracheobronchial area of a patient by designing a cylindrically thickened piston-shaped area 10a near the distal end of the catheter tube. The piston-shaped area is then intended to have a length of at least 1.25 mm with at least approximately 5.1 mm. The outer cross section of the catheter tube that tapers toward the distal end also prevents clogging of the end of the lumen with secretion. This could be advantageous, particularly with large cross sections of lumen 13 of catheter tube 10 of a suction catheter according to FIG. 1. On the other hand, the mere funnel-shaped expansion of the outlet end of the lumen at the distal end of the catheter tube has advantageous effects to prevent the latter from being clogged with secretion.

I claim:

1. A suction catheter for sucking mucus and other fluids out of a tracheobronchial area of a patient which comprises a flexible catheter tube having at least one through lumen extending from a proximal end to a distal end of said tube, the proximal end of the tube being connectable with a connector, ventilation openings formed in the catheter tube in a vicinity of the distal end, said ventilation openings extending radially into the lumen, a distal outlet opening being formed at the distal end and being enlarged with respect to the cross section of the lumen, and a thickened area in the shape of a cylindrical piston being formed in a wall portion of the catheter tube that extends in a zone between the ventilation openings and the distal end; said lumen being expanded in the manner of a funnel towards the distal end of the catheter tube and two transition zones adjoining ends of a thickened area, one transition zone tapering towards the distal end and the other transition zone tapering towards the proximal end wherein in order to establish sizes of the suction catheter, measured in CH (Charr) according to the ISO standard, outside diameter (DK) of the cylindrical piston formed by the thickened area of the catheter tube is used to determine the standard size and the diameter DI of the through lumen used for suction is then determined from the standard size.

2. A suction catheter for sucking mucus from the tracheobronchial system of a patient, comprising a flexible catheter tube having a proximal end and a distal end and at least one through lumen extending from the proximal end to the distal end, ventilation openings formed in one zone of the catheter tube near the distal end, said ventilation openings leading into the lumen, another zone of the catheter tube including a thickened area located between the ventilation openings and the distal end, the thickened area having a shape of a cylindrical piston with a central cylindrical outside wall and proximal and distal transition zones adjacent to the central cylindrical outside wall, said cylindrical outside wall having a predetermined length of approximately 1.25 to 5.1 mm and the ventilation openings being formed adjacent to the proximal transition zone at a predetermined distance (f) from the central cylindrical outside wall, length (a) of the central cylindrical outside wall being sufficient to permit guidance of the suction tube when the catheter is introduced into the tracheobronchial system of a patient.

3. A suction catheter according to claim 2, wherein the predetermined distance (f) is less than 7 mm between the ventilation openings and the central cylindrical outside wall.

4. A suction catheter according to claim 2, wherein the predetermined length of the central cylindrical outside wall is approximately the same as the diameter (DK) of the thickened area of the catheter tube.

5. A suction catheter according to claim 2, wherein length (a) of the central cylindrical outside wall is at least twice the diameter (DI) of the lumen.

6. A suction catheter according to claim 2, wherein the ventilation openings are positioned at a distance (LF) of approximately 6 mm to 16 mm from the distal end of the flexible catheter tube.

7. A suction catheter for sucking mucus from the tracheobronchial system of a patient, comprising a flexible catheter tube with a proximal end and a distal end and at least one through lumen extending from the proximal end to the distal end, said catheter tube having ventilation openings near the distal end and the lumen of the catheter tube having a funnel-shaped expansion that extends towards the distal end, at least one notch being formed in a wall of the catheter tube defining the funnel-shaped expansion.

8. A suction catheter according to claim 7, wherein the flexible catheter tube has at least two uniformly distributed notches in the funnel-shaped expansion that extend radially along a portion of the lumen.

9. A suction catheter according to claim 8, wherein the uniformly distributed notches are so formed that they extend axially along a portion of the lumen for the same distance as the funnel-shaped expansion.

10. A suction catheter according to claim 7, wherein the funnel-shaped expansion extends from the distal end of the catheter up to a position in the lumen that is approximately 2 mm to 4 mm away from the distal end.

11. A suction catheter for sucking mucus and other fluids out of a tracheobronchial area of a patient which comprises a flexible catheter tube having at least one through lumen extending from a proximal end to a distal end of said tube, the proximal end of the tube being connectable with a connector, ventilation openings formed in the catheter tube in a vicinity of the distal end, said ventilation openings extending radially into the lumen, a distal outlet opening being formed at the distal end and being enlarged with respect to the cross section of the lumen, and a thickened area in the shape of a cylindrical piston being formed in a wall portion of the catheter tube that extends in a zone between the ventilation openings and the distal end; said lumen being expanded in the manner of a funnel towards the distal end of the catheter tube and two transition zones adjoining ends of a thickened area, one transition zone tapering towards the distal end and the other transition zone tapering towards the proximal end wherein length (a) of the cylindrical piston formed by the thickened area of the catheter tube, for suction catheter sizes of from 8 CH to 18 CH, is between 2 mm and 8 mm.

12. A suction catheter according to claim 11, wherein the funnel, beginning at the distal end has a length (t) of approximately 2 to 4 mm.

13. A suction catheter for sucking mucus and other fluids out of a tracheobronchial area of a patient which comprises a flexible catheter tube having at least one through lumen extending from a proximal end to a distal end of said tube, the proximal end of the tube being connectable with a connector, ventilation openings formed in the catheter tube in a vicinity of the distal end, said ventilation openings extending radially into the lumen, a distal outlet opening being formed at the distal end and being enlarged with respect to the cross section of the lumen, and a thickened area in the shape of a cylindrical piston being formed in a wall portion of the catheter tube that extends in a zone between the ventilation openings and the distal end; said lumen being expanded in the manner of a funnel towards the distal end of the catheter tube and two transition zones adjoining ends of a thickened area, one transition zone tapering towards the distal end and the other transition zone tapering towards the proximal end wherein the through lumen is expanded towards the distal end by at least two axially extending notches uniformly distributed over the circumference of the lumen.

14. A suction catheter according to claim 13, wherein the notches have an axial length (d2) of approximately 2 to 4 mm and a width (d3) less than the diameter of the lumen.

15. A suction catheter for sucking mucus and other fluids out of a tracheobronchial area of a patient which comprises a flexible catheter tube having at least one through lumen extending from a proximal end to a distal end of said tube, the proximal end of the tube being connectable with a connector, ventilation openings formed in the catheter tube in a vicinity of the distal end, said ventilation openings extending radially into the lumen, a distal outlet opening being formed at the distal end and being enlarged with respect to the cross section of the lumen, and a thickened area in the shape of a cylindrical piston being formed in a wall portion of the catheter tube that extends in a zone between the ventilation openings and the distal end; said lumen being expanded in the manner of a funnel towards the distal end of the catheter tube and two transition zones adjoining ends of a thickened area, one transition zone tapering towards the distal end and the other transition zone tapering towards the proximal end wherein the funnel has a length of approximately 2 to 4 mm and the thickened area forms a cylindrical piston having a length (a) for suction catheter sizes from 8 CH to 18 CH between approximately 2 mm and 8 mm.

16. A suction catheter for sucking mucus and other fluids out of a tracheobronchial area of a patient which comprises a flexible catheter tube having at least one through lumen extending from a proximal end to a distal end of said tube, the proximal end of the tube being connectable with a connector, ventilation openings formed in the catheter tube in a vicinity of the distal end, said ventilation openings extending radially into the lumen, a distal outlet opening being formed at the distal end and being enlarged with respect to the cross section of the lumen, and a thickened area in the shape of a cylindrical piston being formed in a wall portion of the catheter tube that extends in a zone between the ventilation openings and the distal end; said lumen being expanded in the manner of a funnel towards the distal end of the catheter tube and two transition zones adjoining ends of a thickened area, one transition zone tapering towards the distal end and the other transition zone tapering towards the proximal end wherein the difference between wall thickness (SK) of the cylindrical piston and wall thickness (SR) of the catheter tube is between 0.4 and 0.6 mm at catheter sizes of 8 CH to 18 CH.

17. A suction catheter for sucking mucus and other fluids out of a tracheobronchial area of a patient which comprises a flexible catheter tube having at least one through lumen extending from a proximal end to a distal end of said tube, the proximal end of the tube being connectable with a connector, ventilation openings formed in the catheter tube in a vicinity of the distal end, said ventilation openings extending radially into the lumen, a distal outlet opening being formed at the distal end and being enlarged with respect to the cross section of the lumen, and a thickened area in the shape of a cylindrical piston being formed in a wall portion of the catheter tube that extends in a zone between the ventilation openings and the distal end; said lumen being expanded in the manner of a funnel towards the distal end of the catheter tube and two transition zones adjoining ends of a thickened area, one transition zone tapering towards the distal end and the other transition zone tapering towards the proximal end wherein wall thickness (SK) of the cylindrical piston is between 0.7 and 1.4 mm at suction catheter sizes from 8 CH to 18 CH and wall thickness (SR) of the catheter tube is between 0.3 and 0.8 mm.

18. A suction catheter for sucking mucus and other fluids out of a tracheobronchial area of a patient which comprises a flexible catheter tube having at least one through lumen extending from a proximal end to a distal end of said tube, the proximal end of the tube being connectable with a connector, ventilation openings formed in the catheter tube in a vicinity of the distal end, said ventilation openings extending radially into the lumen, a distal outlet opening being formed at the distal end and being enlarged with respect to the cross section of the lumen, and a thickened area in the shape of a cylindrical piston being formed in a wall portion of the catheter tube that extends in a zone between the ventilation openings and the distal end; said lumen being expanded in the manner of a funnel towards the distal end of the catheter tube and two transition zones adjoining ends of a thickened area, one transition zone tapering towards the distal end and the other transition zone tapering towards the proximal end wherein a space between (f1) of 2 to 3 mm is provided between the transition zone tapering towards the proximal end and the ventilation openings.

19. A suction catheter for sucking mucus and other fluids out of a tracheobronchial area of a patient which comprises a flexible catheter tube having at least one through lumen extending from a proximal end to a distal end of said tube, the proximal end of the tube being connectable with a connector, ventilation openings formed in the catheter tube in a vicinity of the distal end, said ventilation openings extending radially into the lumen, a distal outlet opening being formed at the distal end and being enlarged with respect to the cross section of the lumen, and a thickened area in the shape of a cylindrical piston being formed in a wall portion of the catheter tube that extends in a zone between the ventilation openings and the distal end; said lumen being expanded in the manner of a funnel towards the distal end of the catheter tube and two transition zones adjoining ends of a thickened area, one transition zone tapering towards the distal end and the other transition zone tapering towards the proximal end wherein the transition zones adjoining the cylindrical piston run at an angle of from about 10° to 10° with respect to a longitudinal axis of the lumen.

20. A suction catheter for sucking mucus and other fluids out of a tracheobronchial area of a patient which comprises a flexible catheter tube having at least one through lumen extending from a proximal end to a distal end of said tube, the proximal end of the tube being connectable with a connector, ventilation openings formed in the catheter tube in a vicinity of the distal end, said ventilation openings extending radially into the lumen, a distal outlet opening being formed at the distal end and being enlarged with respect to the cross section of the lumen, and a thickened area in the shape of a cylindrical piston being formed in a wall portion of the catheter tube that extends in a zone between the ventilation openings and the distal end; said lumen being expanded in the manner of a funnel towards the distal end of the catheter tube and two transition zones adjoining ends of a thickened area, one transition zone tapering towards the distal end and the other transition zone tapering towards the proximal end wherein total length (Lf) of a distal end portion of the catheter tube including the thickened area is made the same length from the ventilation openings to the distal end for suction catheters of sizes 8 CH to 18 CH and is in the range of from about 8 to 12 mm.

21. A suction catheter for sucking mucus and other fluids out of a tracheobronchial area of a patient which comprises a flexible catheter tube having at least one through lumen extending from a proximal end to a distal end of said tube, the proximal end of the tube being connectable with a connector, ventilation openings formed in the catheter tube in a vicinity of the distal end, said ventilation openings extending radially into the lumen, a distal outlet opening being formed at the distal end and being enlarged with respect to the cross section of the lumen, and a thickened area in the shape of a cylindrical piston being formed in a wall portion of the catheter tube that extends in a zone between the ventilation openings and the distal end; said lumen being expanded in the manner of a funnel towards the distal end of the catheter tube and two transition zones adjoining ends of a thickened area, one transition zone tapering towards the distal end and the other transition zone tapering towards the proximal end wherein the cylindrical piston determines by its outside diameter (DK) the size in CH of the suction catheter and the catheter tube has a wall portion abutting the cylindrical portion and extending to the proximal end with an outside diameter (DR) that is reduced relative to the outside diameter (DK) of the cylindrical piston, with the cylindrical piston having a predetermined length such that the cylindrical piston is able to guide the suction catheter when it is introduced into the tracheobronchial area of a patient.

* * * * *